(12) United States Patent
Kamath et al.

(10) Patent No.: US 7,573,978 B2
(45) Date of Patent: Aug. 11, 2009

(54) VARIABLE FEATHERING FIELD SPLITTING FOR INTENSITY MODULATED FIELDS OF LARGE SIZE

(75) Inventors: Srijit Kamath, Gainesville, FL (US); Sartaj Kumar Sahni, Gainesville, FL (US); Jonathan Li, Gainesville, FL (US); Jatinder Palta, Gainesville, FL (US); Sanjay Ranka, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 11/995,303

(22) PCT Filed: Jul. 11, 2006

(86) PCT No.: PCT/US2006/026891

§ 371 (c)(1),
(2), (4) Date: Jan. 10, 2008

(87) PCT Pub. No.: WO2007/008899

PCT Pub. Date: Jan. 18, 2007

(65) Prior Publication Data

US 2008/0240348 A1 Oct. 2, 2008

Related U.S. Application Data

(60) Provisional application No. 60/698,043, filed on Jul. 11, 2005.

(51) Int. Cl.
*A61N 5/10* (2006.01)
(52) U.S. Cl. ........................... 378/65; 378/152
(58) Field of Classification Search ........... 378/64, 378/65, 147–152
See application file for complete search history.

(56) References Cited

U.S. PATENT DOCUMENTS 7,142,635 B2 * 11/2006 Kamath et al. ................ 378/65

FOREIGN PATENT DOCUMENTS

EP 0 673 661 9/1995

(Continued)

OTHER PUBLICATIONS

Dogan, Nesrin, et al., "Automatic Feathering of Split Fields for Step-and-Shoot Intensity Modulated Radiation Therapy", Physics in Medicine and Biology IOP Publishing, vol. 48, No. 9, pp. 1133-1140. 2003.

(Continued)

*Primary Examiner*—Jurie Yun
(74) *Attorney, Agent, or Firm*—Saliwanchik Lloyd & Saliwanchik

(57) ABSTRACT

A method and associated system 300 for delivering intensity-modulated radiation therapy (IMRT) uses variable feathering field splitting for intensity modulated fields of large size. A processor controls a beam-shaping device that splits the radiation beam into a plurality of radiation fields delivered to a patient. The processor in cooperation with the beam-shaping device implements a variable feathering method which includes providing an intensity matrix for the treatment of a patient, the intensity matrix having a plurality of rows and columns for spanning a prescribed radiation field including a prescribed field width. The prescribed width is compared to a maximum field width provided by the radiation treatment system. The intensity matrix is split into a plurality of spatially overlapping intensity submatrices by variably feathering the intensity matrix when the prescribed width exceeds the maximum field width, Radiotherapy is then provided to the patient using a leaf sequencing method to generate the submatrices.

9 Claims, 6 Drawing Sheets

FOREIGN PATENT DOCUMENTS

WO    WO 2005/096788    10/2005

OTHER PUBLICATIONS

Hong, Linda, et al., "IMRT of Large Fields: Whole-Abdomen Irradiation", International Journal of Radiation Oncology Biology Physics, vol. 54, No. 1, pp. 278-289. 2002.

Wu, Qiuwen, et al., "Dynamic Splitting of Large Intensity-Modulated Fields", Physics in Medicine and Biology IOP Publishing, vol. 45, pp. 1731-1740. 2000.

Wu, Xiadong, "Efficient Algorithms for Intensity Map Splitting Problems in Radiation Therapy", Computing and Combinatorics 11th Annual International Conference, Cocoon 2005 Proceedings.

Dogan, Nesrin, et al., "A Modified Method of Planning and Delivery for Dynamic Multileaf Collimator Intensity'Modulated Radiation Therapy", International Journal of Radiation Oncology Biology Physics, , vol. 47, No. 1, pp. 241-245. 2000.

Kamath, Srijit, et al., "Optimal Field Splitting for Large Intensity-Modulated Fields", Medical Physics AIP, Melville, NY, vol. 31, No. 12, pp. 3314-3323. 2004.

Convery, D.J., et al., "The Generation of Intensity-Modulated Fields for Conformal Radiotherapy by Dynamic Collimation", Physics in Medicine and Biology, vol. 37, No. 6, pp. 1359-1374. 1992.

* cited by examiner

VARIABLE FEATHERING FIELD SPLITTING FOR INTENSITY MODULATED FIELDS OF LARGE SIZE

CROSS-REFERENCE TO RELATED APPLICATIONS

This application is a §371 national stage entry of International Application No. PCT/U.S.2006/026891, filed Jul. 11, 2006, which claims priority to U.S. Provisional Application No. 60/698,043, filed Jul. 11, 2005, both of which are hereby incorporated by reference.

STATEMENT REGARDING FEDERALLY SPONSORED RESEARCH OR DEVELOPMENT

The United States Government has certain rights to this invention pursuant to NIH Grant/Contract No. LM06659-03.

FIELD OF THE INVENTION

The invention relates to radiation therapy devices, and more particularly, to a system and methods for efficiently and more safely delivering split radiation field treatment to a patient.

BACKGROUND

A radiation therapy device typically includes a radiation delivery device mounted to a gantry that is swiveled around a horizontal axis of rotation in the course of a radiation therapy treatment. The radiation delivery device generally delivers a high energy radiation beam. During treatment, the radiation beam is directed towards a patient lying in the isocenter of the gantry rotation.

The device thus normally includes a radiation source, such as a linear accelerator, for supplying the high energy radiation beam. The high energy radiation beam is typically an electron beam or an X-ray beam.

To control the radiation emitted toward a given object, a beam shielding device, such as a plate arrangement or a collimator, is typically provided in the trajectory of the radiation beam between the radiation source and the patient. A collimator is a computer-controlled mechanical beam shielding device which generally includes multiple leaves, for example, a plurality of relatively thin plates or rods, typically arranged as opposing leaf pairs. The plates are formed from a relatively dense and radiation impervious material and are generally independently positionable to size and shape of the radiation beam. These leaves move over the tissue being radiated, thus blocking out some areas and filtering others to vary the beam intensity and precisely distributing the radiation dosage.

A multileaf collimator (MLC) is an example of a multileaf beam shielding device that can accurately and efficiently adjust the size and shape of the radiation beam. The size and shape of a radiation beam is designed during the treatment planning process. This is useful for both intensity modulated radiation treatment (IMRT) and three-dimensional conformal radiation therapy (3D CRT).

Traditional radiotherapy utilizes uniform beams of radiation, producing a uniform distribution of dose throughout the irradiated volume, which includes the target volume. This ensures the target is adequately covered, but does little or nothing to avoid often critical surrounding structures. With , the beams of radiation are made to be intentionally non-uniform. In this manner, the dose distribution can be shaped to reduce or eliminate radiation to surrounding structures. As a result, is increasingly used to treat large volumes because can deliver more conformal radiation while sparing the surrounding normal tissue.

Monitor unit (MU) efficiency is a commonly used measure of beam efficiency. MU efficiency is defined as the efficiency with which the incident radiation results in dose being in absorbed in the target region of a patient. A consequence of low MU efficiency is an increase in leakage radiation that reaches the surrounding (normal) tissue of the patient.

There are several components of a successful program. The first is a process referred to as "inverse planning." Inverse planning utilizes a mathematical algorithm to optimize the intensity of the various beams. This optimization process typically is highly computer intensive.

The second component is a process to convert the intensity distributions obtained, often referred to cumulatively as a fluence map, into a series of MLC leaf movements. This is referred to as "leaf sequencing." Many device-specific factors must be accounted for in this process. These factors include radiation leakage through and between the leaves, leaf speed, dose rate, and the "tongue-and-groove" effect.

can be performed either while the beam is on, which is referred to as dynamic multileaf collimator (DMLC) delivery, or by turning the beam off while the leaves move to their next position, which is referred to as segmented multileaf collimator (SMLC) delivery. The beam shielding device defines a field on the object to which a prescribed amount of radiation is to be delivered. The usual treatment field shape results in a three-dimensional treatment volume which includes segments of normal tissue, thereby limiting the dose that can be given to the target, such as a tumor. The dose delivered to the tumor can be increased, thereby decreasing the treatment time so that the amount of dose delivered to the normal surrounding tissue is decreased. Although current leaf sequencing algorithms have reduced somewhat the radiation level reaching surrounding normal tissue as compared to traditional uniform beams of radiation, these leaf sequences have not provided optimal MU efficiency.

Most treatments are administered with conventional MLC systems that are typically available on commercial linear accelerators. The MLC systems vary in design but each version has certain mechanical limitations, such as maximum leaf over-travel which limits the attainable width of the radiation beam.

It is sometimes necessary to expose large areas of the body of a patient to radiation. If the size of the required radiation field is larger than the maximum attainable width provided by the radiation delivery system, such as in the case of a large tumor, the entire radiation field cannot be exposed at one time by the radiation system. This necessitates that a large field be split into a plurality of abutting field portions, such as 2 or 3 fields portions, where the respective field portions are delivered one at a time. This process is known as feathering.

Feathering splits the overall field into field portions having equal width. For example, available field-splitting algorithms split the field either near the middle of the field along an arbitrarily-chosen straight line, or with a pre-defined constant overlap region for feathering. Due to concerns of increased whole body dose in delivery, the problem of MU efficiency in field splitting needs to be addressed.

SUMMARY OF THE INVENTION

The invention is directed to a radiation delivery system and method which reduces the total monitor units (MUs) used to treat patients requiring large radiation fields. The phrase "large radiation field" is defined herein as a prescribed radiation field width determined by a dose optimization algorithm that exceeds the maximum attainable beam width provided by the radiation delivery system, such as the large field required, for example, in the treatment of certain neck and back tumors.

A method and associated apparatus for delivering intensity-modulated radiation therapy (IMRT) according to the invention uses variable feathering field splitting for intensity modulated fields of large size. The method includes the steps of providing an intensity matrix for the treatment of a patient, the intensity matrix having a plurality of rows and columns for spanning a prescribed radiation field including a prescribed field width. The intensity matrix is generally determined by a medical professional (radiologist or medical physicist) during the planning step. The prescribed field width is compared to a maximum field width provided by the radiation treatment system. The intensity matrix is split into a plurality of spatially overlapping intensity submatrices when the prescribed width exceeds the maximum field width, wherein the splitting comprises variably feathering the intensity matrix. Radiotherapy is then provided using a leaf sequencing method to generate the submatrices.

BRIEF DESCRIPTION OF THE DRAWINGS

A better understanding of the present invention can be obtained when the following detailed description is considered in conjunction with the following drawings in which.

DETAILED DESCRIPTION

Figure 1:
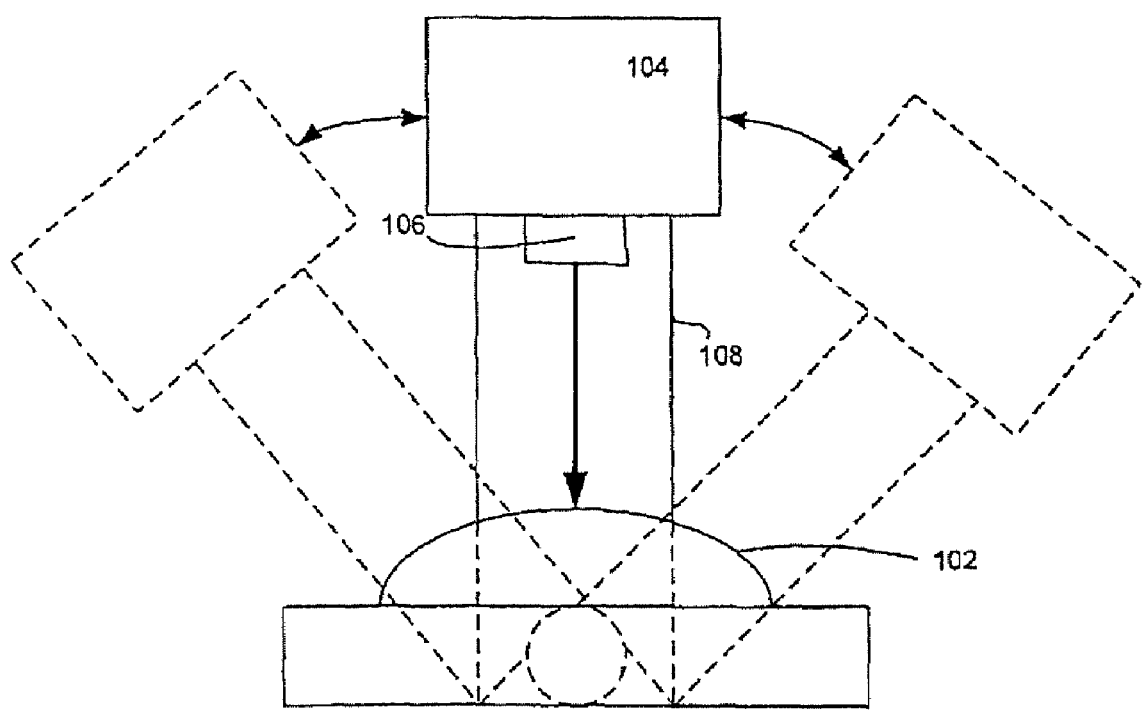
FIG. 1 is a schematic diagram of a system for delivering radiation treatment to a patient, according to one embodiment of the present invention.

FIG. 1 is a schematic diagram a system 100 for delivering radiation treatment to a patient 102 which can be used with the present invention which comprises variable feathering field splitting for intensity modulated fields of large size. The system 100 illustratively includes a radiation source 104 for providing a radiation beam and a beam-shaping device 106 interposed between the radiation source 104 and the patient 102 for shaping the radiation beam.

The radiation source 104, more particularly, can provide electron, photon, or other radiation useful for treating cancer or other disease. For example, as described in Published U.S. Application No. 20050148841 entitled "LEAF SEQUENCING METHOD AND SYSTEM" by the present inventors, the radiation source 104 can be an electron accelerator for delivering an electron beam. As illustrated, the radiation source 104 is mounted upon a gantry 108 that rotates upon a fixed axis so as to permit the position of the radiation source to change relative to the patient 102.

Figure 2:
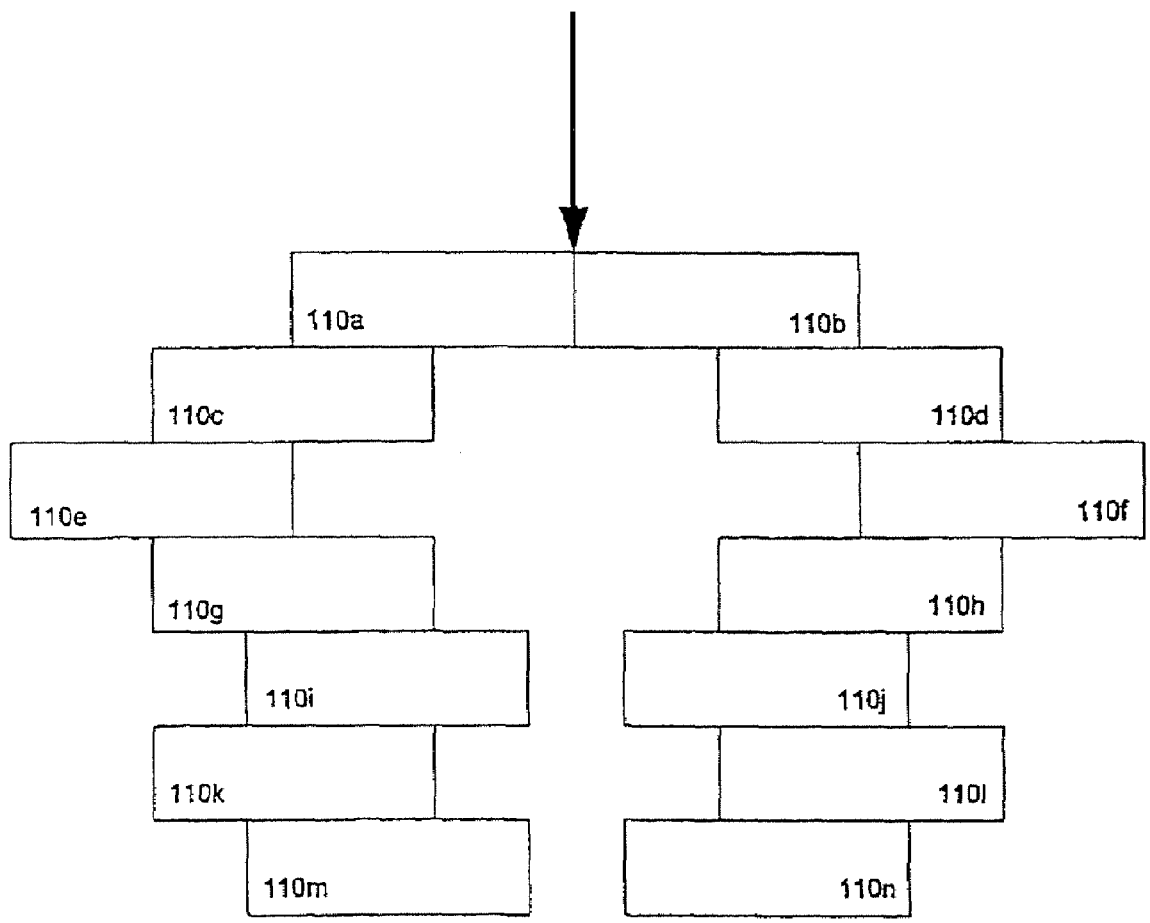
FIG. 2 is a schematic diagram of a beam-shaping device incorporated in a system for delivering radiation treatment to a patient, according to another embodiment of the present invention.

Referring additionally now to FIG. 2, the beam-shaping device 106 interposed between the radiation source 104 and the patient 102 illustratively is shown comprising a plurality of opposing plates or leaves 110a-n that are substantially impervious to the radiation emitted by the radiation source. The leaves 110a-n can be moved by a drive unit (not shown) in a substantially horizontal motion relative to one another and substantially perpendicular to the radiation beam. The movement permits the plurality of leaves 110a-n to be aligned and realigned relative to one another and the radiation beam. Each such alignment comprises a leaf sequence that changes the size and shape of the radiation beam, as further described in Published U.S. Application No. 20050148841. Accordingly, the leaf sequences determine the dimensions of a field on a designated region of the patient 102 to which a prescribed amount of radiation is to be delivered.

The beam-shaping device 106 can be an MLC. More particularly, the beam-shaping-device can comprise a segmented MLC. Alternatively, the beam-shaping device can comprise a dynamic MLC.

Figure 3:
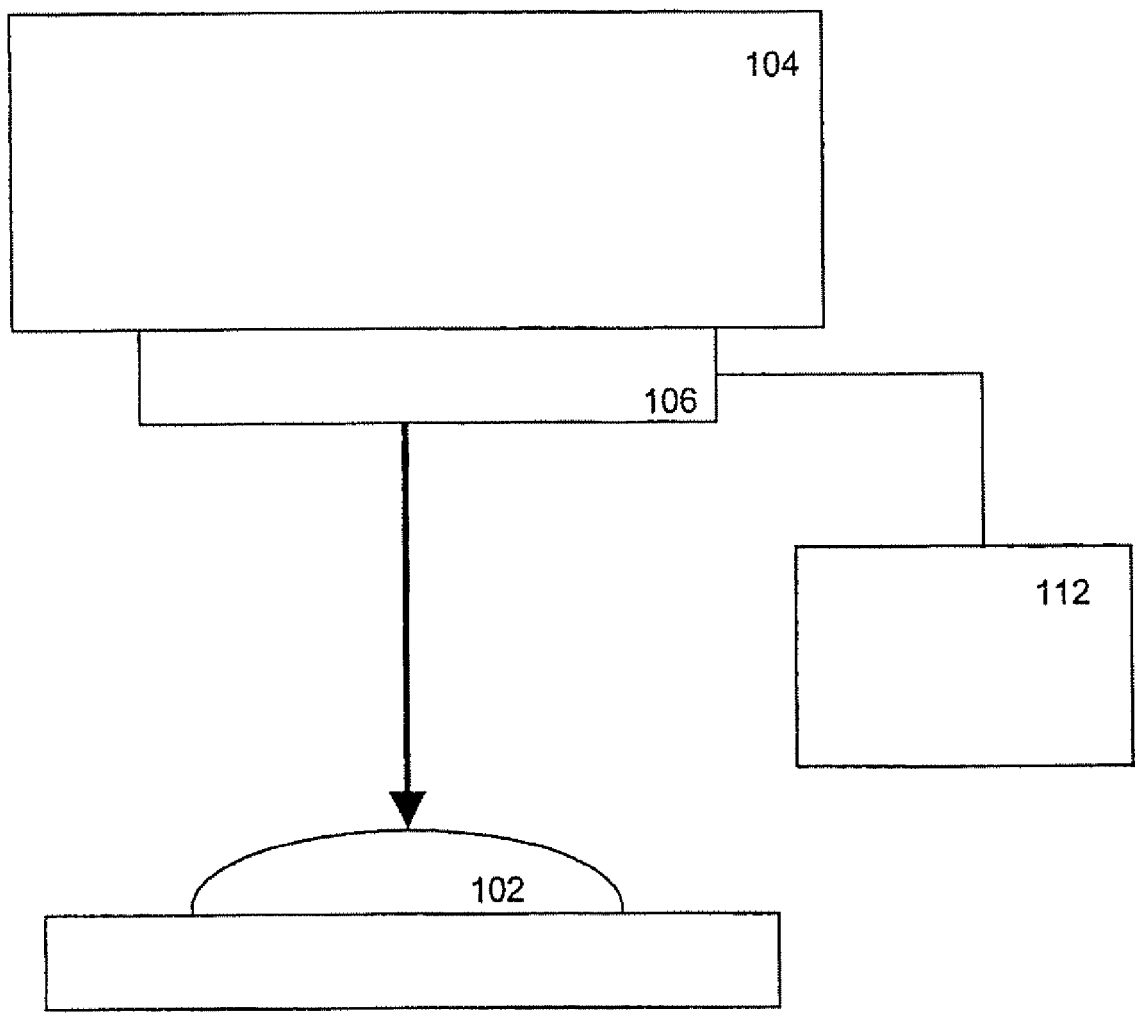
FIG. 3 is a schematic diagram of a system for delivering radiation treatment to a patient, according to still another embodiment of the present invention.

Referring additionally now to FIG. 3, the system 300 for delivering radiation treatment to a patient 102 illustratively includes a processor or other computing device in communication with the beam-shaping device 106. As described herein, the processor 112 can control the beam-shaping device 106 so that the beam-shaping device splits the radiation beam into a plurality of radiation fields that are delivered to the patient. The radiation beam, more particularly, is split so as to substantially minimize at least one of a total therapy time and a total number of leaf sequences in delivering a predetermined dosage of radiation to the patient. As defined herein, "a substantial minimization of the total therapy time" denotes a reduction of the therapy time to no more 20 percent, and more preferably no more than 10 percent, over an absolute minimum. Similarly, minimization of the total number of leaf sequences denotes no more than 20 percent, and more preferably no more than 10 percent, over the absolute minimum.

The processor 112 can connect to a standard input-output (I/O) device such as a keyboard. Thus, the processor can be programmed, for example, by a therapist according to instructions dictated by an oncologist or medical physicist. Processor 112 can also control the beam-shaping device 106 by executing and delivering instructions to the drive units (not shown) that align the opposing plates or leaves 110a-n so that different leaf sequences are effected according to the programmed instructions.

A method and associated apparatus for delivering intensity-modulated radiation therapy (IMRT) using variable feathering field splitting for intensity modulated fields of large size includes the steps of providing an intensity matrix for the treatment of a patient, the intensity matrix having a plurality of rows and columns for spanning a prescribed radiation field including a prescribed field width. The intensity matrix is generally determined by a medical professional during the planning step. The prescribed width is compared to a maximum field width provided by the radiation treatment system. The intensity matrix is split into a plurality of spatially overlapping intensity submatrices when the prescribed width exceeds the maximum field width.

Unlike previous feathering work which discloses a predefined constant overlap region for feathering, being a constant overlap of up to about a 2 cm width throughout the field, the overlap variable region according to the invention is a non-constant width derived from "variably feathering" the intensity matrix to derive corresponding submatrices. The variable feathering calculation as described herein is preferably based on minimizing MUs and can be implemented by a field splitting module integrated into treatment planning software. Radiotherapy is then provided using a leaf sequencing method to generate the submatrices.

As noted above, previous feathering work utilized a constant overlap width of no more than about 2 cm. Variable feathering according to the invention can utilize an overlap that ranges from zero to the maximum allowable width of a field (which is currently generally about 14 cm). Suppose the intensity matrix is a large matrix having a width=20 cm, and the maximum allowed field width is 14 cm. With conventional fixed width feathering of 2 cm, one possible arrangement is to have the first split submatrix have a width of 12 cm, with the second submatrix having a width of width 10 cm, and have their respective two central columns (2 cm) overlap (feathering=2). If any of the submatrices are made wider, the overlap would have to be wider and this is not allowed in fixed width feathering. In contrast, using variable feathering according to the invention, it is possible for example to split the large intensity matrix into two submatrices each of width 14 cm with an overlap of the 8 central columns (8 cm=14 cm+14 cm−20 cm).

By allowing wider overlaps according to the invention, the use of smaller overlaps is not discarded, since algorithms according to the invention pick the best overlap for MU efficiency. The best overlap may be wide or narrow. Earlier methods allowed only no or narrow and constant overlaps.

The ability to utilize wider overlaps provides higher MU efficiency. A simplified explanation for the MU efficiency improvement is that the presence of a wider overlap region gives a bigger time/space "window" of treatment delivery during a transition which may be made from neighboring subfields, such as between the left and right subfield in the case of two subfields. The larger window provided presents greater opportunities for an efficient split. Experimentally, as noted in the Examples, the improvement obtained averaged 19% compared to a commercial system. Earlier methods disclosed by the inventors (straight line split and 2 cm feathering) had given a little over 10% improvement over a conventional t commercial system. Clearly, allowing the wider overlap provides an improvement in MU efficiency.

The invention thus treats the most general field splitting problem for segmental MLCs. In this generalized model, the only constraint is that the subfields resulting from the split are each required to have a width≦w sample points, where w is the maximum allowable field width provided by the radiation system used. Field width is loosely defined as the number of columns over which non-zero fluence values span. There may be bixels (2D pixels) that receive parts of their desired fluence from two subfields.

Figures 4, 5:
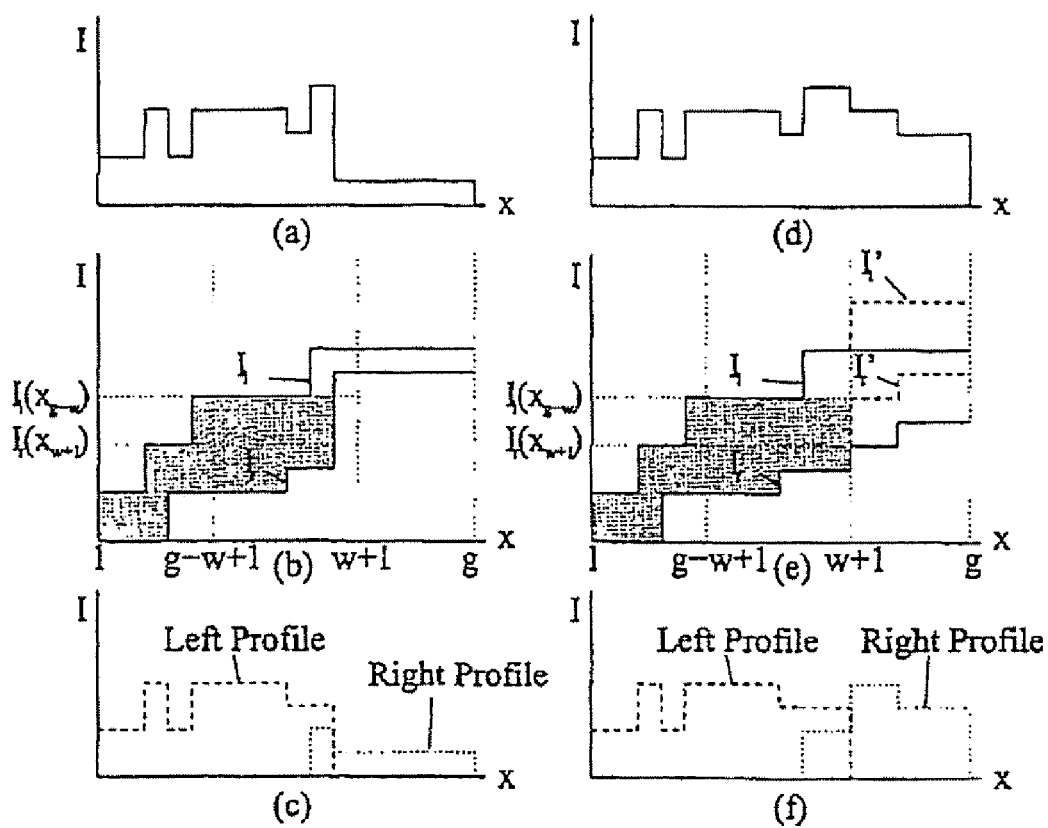
FIG. 4 shows a fluence matrix and fields resulting from variably feathering along a non-constant column of the intensity matrix according to the invention.
FIG. 5 shows (a) a single pair profile, (b) a plan $(I_l, I_r)$, for profile I of (a), is obtained using Algorithm SINGLEPAIR and is constructed without taking field width constraints into account. It can be delivered for $I_l(x_{g-w})$ MUs in the left field (shaded) and the remainder in the right field; (c) the left and right profiles resulting from the split generated by Algorithm S2G. This split is delivered in optimal time using the plan $(I_l, I_r)$; d) a single pair profile; (e) plan $(I_l, I_r)$, for profile I of (d), is obtained using Algorithm SINGLEPAIR and is constructed without taking field width constraints into account. $(I_l, I_r)$ is the modified plan obtained using Algorithm S2G and can be delivered for $I_l(x_{g-w})$ MUs in the leftfield (shaded) and the remainder in the right field; (f) the left and right profiles resulting from the split generated by Algorithm S2G. This split is delivered in optimal time using the plan $(I_l, I_r)$.

FIG. 4 shows a fluence matrix and fields resulting from variably feathering along a non-constant column of the intensity matrix according to the invention. A generalized split with w=5 is shown. The matrix on the left is split into the two matrices on the right. In the first row there is feathering along column 3. The second row feathers along columns 4 and 5 and the third row feathers along columns 3, 4 and 5. The widths of the fields resulting from the split are shaded in FIG. 4. It can be shown that the inventive algorithm for field splitting is optimal in MU efficiency (See attached papers in Appendix). Tests with 32 clinical matrices showed that the inventive optimal field splitting algorithm reduces total MUs by an average of 19% and up to 45% compared to the algorithm that splits a field in the middle.

The invention is described in further detail below along with some preferred embodiments for several system arrangements.

1. Single Leaf Pair Profile

Let $I(x_i)$ be the discretized fluence profile obtained from the optimizer that gives the fluence values at sample points $x_1$, $x_2, \ldots, x_m$ for a single leaf pair. A profile $I(x_i)$ is simply referred to herein as profile I. When the left leaf is placed so that it shields exactly the points $x_1, x_2, \ldots, x_i$, it will be said that the left leaf is positioned at $x_{i+1}$. In particular, the point $x_{i+1}$ is not shielded by it. When the right leaf is placed so that it shields exactly $x_{i+1}, x_{i+2}, \ldots x_m$, it will be said that the right leaf is positioned at $x_{i+1}$. The problem of delivering the exact profile I using a single field has been extensively studied. Ma et. al. (Ma L, et. al. An optimized leaf-setting algorithm for beam intensity modulation using dynamic multileaf collimators. Phys. Med. Biol. 43:1629, 1998) provided an O(m) algorithm for the problem such that MU is minimized. Kamath et. al. (Kamath S, et. al. Leaf sequencing algorithms for segmented multileaf collimation. Phys. Med. Biol. 48:307, 2003) also described the algorithm (Algorithm SINGLEPAIR) and gave an alternate proof that it obtains a plan $(I_l, I_r)$ with optimal therapy time for I. Here, $I_l(x_i)$ and $I_r(x_i)$ denote, respectively, the number of MUs after which the left and right leaves pass point $x_i$ during the left to right sweep. Let $\delta_i = I(x_i) - I(x_{i-1})$, where $I(x_0) = 0$ and $I(x_{m+1}) = 0$. Let inc1, inc2, ..., incq be the indices of the points at which $I(x_i)$ increases, i.e., $I(x_{inci}) > I(x_{inci-1})$ and let dec1, dec2, ..., decr be the indices of the points at which $I(x_i)$ decreases, i.e., $I(x_{deci}) < I(x_{deci-1})$. The optimal therapy time for I, S1(I), is given by Lemma 1.

Lemma 1.

$$S1(I) = \sum_{i=1}^{q} \delta_{inci} = -\sum_{i=1}^{r} \delta_{deci}.$$

The following lemma is useful in proving the optimality of the algorithm developed and is stated without proof.

Lemma 2. The following is true of all treatment plans delivered using one or more fields:
1. If $I(x_{i-1}) > I(x_i)$, the right leaf must be positioned at $x_i$ for at least $I(x_{i-1}) - I(x_i) = -\delta_i$ MUs in every plan for I.
2. If $I(x_{i-1}) < I(x_i)$, the left leaf must be positioned at $x_i$ for at least $I(x_i) - I(x_{i-1}) = \delta_i$ MUs in every plan for I.

Consider a fluence profile I (FIG. 5(a)). $(I_l, I_r)$ is its optimal plan generated using Algorithm SINGLEPAIR. Suppose that w<g≦2w, so that the field needs to be split into two. Call the fields resulting from a split as the left and the right fields, labeling them to denote their respective positions. It is possible that the left field stretches as far to the right and including sample point $x_w$ and that the right field stretches as far to the left and including $x_{g-w+1}$. Examine the unidirectional leaf trajectories in the plan $(I_l, I_r)$ (FIG. 5b). Clearly, the plan cannot be delivered as such because of the field width constraint. The strategy according to the invention is to follow the plan $(I_l, I_r)$ to the maximum extent possible while delivering it using two fields. There are two cases. In the first case, $I_l(x_{g-w}) \leq I_r(x_{w+1})$ (as is the case in FIG. 5(b)), the left field can be treated using the plan $(I_l, I_r)$ for $I_l(x_{g-w})$ MUs. At the end of this time, the left leaf will be at $x_t \leq x_{g-w}$ (and can immediately move to $x_{g-w+1}$) and the right leaf will immediately be positioned in the range $[x_{g-w+1}, x_{w+1}]$ (since $I_r(x_{w+1}) \geq I_l(x_{g-w})$). Since both resulting leaf positions are within the range permissible for the right field ($[x_{g-w+1}, x_g]$), treatment using the plan $(I_l, I_r)$ in the left field is stopped, move to the right field and continue the treatment in the right field. No MU increase is needed due to field splitting.

In the second case, $I_l(x_{g-w}) > I_r(x_{w+1})$. FIG. 5(d) shows a profile I and FIG. 5(e) shows the plan $(I_l, I_r)$ for which this is the case. The left field can be treated using the plan $(I_l, I_r)$ for $I_l(x_{g-w})$ MUs. The left leaf can move to $x \geq x_{g-w+1}$ at this time and the remainder of the plan can be delivered using the right field as in the first case. However, the right leaf will have to cross the right end of the left field ($x_{w+1}$) when $I_r(x_{w+1}) < I_l(x_{g-w})$ MUs have been delivered in the plan $(I_l, I_r)$. Since this is not possible, the right leaf is stopped at the point $x_{w+1}$ till $I_l(x_{g-w})$ MUs are delivered in the left field. As a result of this, the right leaf profile will be raised by $I_l(x_{g-w}) - I_r(x_{w+1})$ MUs for $x \geq x_{w+1}$. To maintain constant difference between the profiles, the left leaf profile is also raised by $I_l(x_{g-w}) - I_r(x_{w+1})$ MUs for $x \geq x_{w+1}$. Call the modified plan $(I'_l, I'_r)$. When $I_l(x_{g-w})$ MUs are delivered, the left leaf can move to the right field and the remainder of the plan $(I'_l, I'_r)$ is delivered using the right field. The plan $(I'_l, I'_r)$, has an increase in total therapy time by $I_l(x_{g-w}) - I_r(x_{w+1})$ compared to $(I_l, I_r)$. In FIG. 5(e), the horizontal dotted line at $I_l(x_{g-w})$ corresponds to the time at which the transition is made from the left to the right field. FIG. 5(f) shows the fluence profiles delivered in the left and right fields as a result of this split. Algorithm S2G summarizes the general method.

Algorithm S2G
Find plan $(I_l, I_r)$ for I using Algorithm SINGLEPAIR, ignoring the field width constraints.
If $I_l(x_{g-w}) > I_r(x_{w+1})$, raise the left and right leaf profiles by $I_l(x_{g-w}) - I_r(x_{w+1})$ for $x > x_w$. Otherwise, do not modify the plan. Call the resulting plan $(I'_l, I'_r)$.
Treat the left field using the plan $(I'_l, I'_r)$ for $I_l(x_{g-w})$ MUs. Then switch to the right field and continue treatment with $(I'_l, I'_r)$.

The following theorem is stated without proof.

Theorem 1. Algorithm S2G generates generalized field splits that are optimal in total therapy time. The optimal total therapy time of the split generated by Algorithm S2G is $S1(I) + \max\{0, I_l(x_{g-w}) - I_r(x_{w+1})\}$, where $S1(I)$ is found by ignoring the field width constraints.

2. Multiple Leaf Pair Profiles

Suppose the fluence matrix I consists of n rows and m columns. Denote the rows of I by $I_1, I_2, \ldots I_n$. For the case where I is deliverable using one field, the leaf sequencing problem has been well studied. The algorithm that generates optimal therapy time schedules for multiple leaf pairs (Algorithm MULTIPAIR, Kamath S, et. al. Leaf sequencing algorithms for segmented multileaf collimation. Phys. Med. Biol. 48:307, 2003) applies algorithm SINGLEPAIR independently to each row $I_i$ of I. Without loss of generality assume that the least column index containing a non zero element in I is 1 and the largest column index containing a non zero element in I is g. If g>w, the profile will need to be split. Let $\{(I_{1l}, I_{1r}), (I_{2l}, I_{2r}), \ldots, (I_{nl}, I_{nr})\}$ be the schedule (set of plans of all leaf pairs) generated by Algorithm MULTIPAIR for delivering the profile I. The points $x_1, x_2, \ldots, x_w$, need to be completely treated in the left field. Let k be an index of a leaf pair for which the left leaf is slowest in reaching $x_{g-w+1}$ during the left to right sweep, i.e., $I_{kl}(x_{g-w}) = \max_{1 \leq i \leq n}\{I_{il}(x_{g-w})\}$. For each leaf pair i, compare $I_{ir}(x_{w+1})$ with $I_{kl}(x_{g-w})$. If $I_{kl}(x_{g-w}) \leq I_{ir}(x_{w+1})$, then the profile of leaf pair i remains unaltered. If $I_{kl}(x_{g-w}) > I_{ir}(x_{w+1})$, then the right leaf of pair i will have to stop at $x_{w+1}$ till the left leaf of pair k arrives at $x_{g-w+1}$. As a result, the left and right leaf profiles of pair i get raised by $I_{kl}(x_{g-w}) - I_{ir}(x_{w+1})$ for $x > x_w$. Call the resulting schedule $\{(I'_{1l}, I'_{1r}), (I'_{2l}, I'_{2r}), \ldots, (I'_{nl}, I'_{nr})\}$. When the left leaf of pair k reaches $x_{g-w+1}$ in this schedule, stop treatment of the left field and move to the right field. The remainder of the schedule is delivered in the right field. The method is described in Algorithm M2G. The optimal total therapy time for the split generated by Algorithm M2G is $\max_j\{S1(I_j) + \max\{0, I_{kl}(x_{g-w}) - I_{jr}(x_{w+1})\}\}$.

Algorithm M2G
Find the schedule $\{(I_{1l}, I_{1r}), (I_{2l}, I_{2r}), \ldots, (I_{nl}, I_{nr})\}$ for I using Algorithm MULTIPAIR, ignoring the field width constraints.
Let $I_{kl}(x_{g-w}) = \max_{1 \leq i \leq n}\{I_{il}(x_{g-w})\}$.
For each leaf pair i do step 4.
If $I_{kl}(x_{g-w}) > I_{ir}(x_{w+1})$ raise the left and right profiles of pair i by $I_{kl}(x_{g-w}) - I_{ir}(x_{w+1})$ for $x > x_w$. Otherwise, do not modify the plan for pair i.
Call the resulting schedule $\{(I_{1l}, I_{1r}), (I_{2l}, I_{2r}), \ldots, (I_{nl}, I_{nr})\}$.
Treat the left field using the schedule $\{(I_{1l}, I_{1r}), (I_{2l}, I_{2r}), \ldots, (I_{nl}, I_{nr})\}$ for $I_{kl}(x_{g-w})$ MUs. Then switch to the right field and continue treatment with this schedule.

Lemma 3. $M2G(I) \geq \max_j\{S1(I_j) + \max\{0, I_{kl}(x_{g-w}) - I_{jr}(x_{w+1})\}\}$, where $S1(I_j)$ is found by ignoring the field width constraints and k is as in Algorithm M2G.

3. For each row j, it is shown that $$M2G(I) \geq S1(I_j) + \max\{0, I_{kl}(x_{g-w}) - I_{jr}(x_{w+1})\}). \text{ It follows that}$$

$$M2G(I) \geq \max_j\{S1(I_j) + \max\{0, I_{kl}(x_{g-w}) - I_{jr}(x_{w+1})\}\}.$$

$$I_{kl}(x_{g-w}) - I_{jr}(x_{w+1}) \leq 0. \qquad (a)$$

In this case $\max\{0, I_{kl}(x_{g-w}) - I_{jr}(x_{w+1})\} = 0$. It is easy to see that, $M2G(I) \geq S1(I_j)$.

4.

$$I_{kl}(x_{g-w}) - I_{jr}(x_{w+1}) > 0.$$

Let $\delta j i = I_j(x_i) - I_j(x_{i-1})$. Let L and R, respectively, denote the left and right profiles resulting from a generalized split. Let $L_j$ denote the jth row of L and let $R_j$ denote the jth row of R. Let $\delta 1_{ji} = L_j(x_i) - L_j(x_{i-1})$ and let $\delta 2_{ji} = R_j(x_i) - R_j(x_{i-1})$. The optimal total therapy time of the split is $M1(L) + M1(R)$. Due to the field width constraint, the points $x_1, x_2, \ldots, x_{g-w}$, can only be exposed in L. So, $L_j(x_i) = I_j(x_i)$, $1 \leq i \leq g-w$, and therefore, $\delta 1_{ji} = \delta_{ji}$, $1 \leq i \leq g-w$. Similarly, $\delta 2_{ji} = \delta_{ji}$, $w+2 \leq i \leq g$. Let the number of MUs for which the left leaf of leaf pair j stops at point $x_i$ in optimal schedules for L and R, respectively, be $\hat{L}_{jl}(x_i)$ and $\hat{R}_{jl}(x_i)$ and the number of MUs for which the right leaf stops at point $x_i$ in optimal schedules for L and R, respectively, be $\hat{L}_{jr}(x_i)$ and $\hat{R}_{jr}(x_i)$.

Since the points 1, 2, . . . , g−w, can only be exposed in L, for each j, $M1(L) \geq \Sigma_{1 \leq i \leq g-w} \hat{L}_{kl}(x_i) \geq \Sigma_{\delta 1_{ki} \geq 0, 1 \leq i \leq g-w} \delta 1_{ki}$
(Lemma 2)$= \Sigma_{\delta_{ji} > 0, 1 \leq i \leq g-w} \delta_{ki} - \Sigma_{\delta_{ji} < 0, i \leq w+1} \delta_{ji} +$
$\Sigma_{\delta_{ji} < 0, i \leq w+1} \delta_{ji} = I_{kl}(x_{g-w}) - I_{jr}(x_{w+1}) + \Sigma_{\delta_{ji} < 0, i \leq w+1}$
$(-\delta_{ji})$.

Similarly, from Lemma 1 and the fact that the points w+1, w+2, . . . , g, can only be exposed in $R_j$, for each j, $M1(R_j) \geq S1(R_j) \geq \Sigma_{i > w+1} \hat{R}_{jr}(x_i) \geq \Sigma_{\delta 2_{ji} < 0, i > w+1} (-\delta 2_{ji})$(Lemma 2)$= \Sigma_{\delta_{ji} < 0, i > w+1} (-\delta_{ji})$. Adding, $M1(L) + M1(R) \geq \Sigma_{\delta_{ji} < 0, i > w+1}(-\delta_{ji}) + \Sigma_{\delta_{ji} < 0, i \leq w+1}(-\delta_{ji}) +$
$I_{kl}(x_{g-w}) - I_{jr}(x_{w+1}) = S1(I_j) + I_{kl}(x_{g-w}) - I_{jr}(x_{w+1})$.

Therefore, $M2G(I) \geq S1(I_j) + I_{kl}(x_{g-w}) - I_{jr}(x_{w+1})$.

Theorem 2. Algorithm M2G generates generalized field splits that are optimal in total therapy time.

5. Follows from Lemma 3 and the fact that the total therapy time of the split generated by Algorithm M2G is $\max_j \{ S1(I_j) + \max \{ 0, I_{kl}(x_{g-w}) - I_{jr}(x_{w+1}) \} \}$.

Although the invention has been described above relative to splitting a profile into two (2) intensity matrices in an optimal manner, the invention more generally splits a profile into a plurality (two or more) intensity matrices in an optimal manner. Splitting a profile into three (3) intensity matrices is described below.

Splitting a Profile into Three

Figure 6:
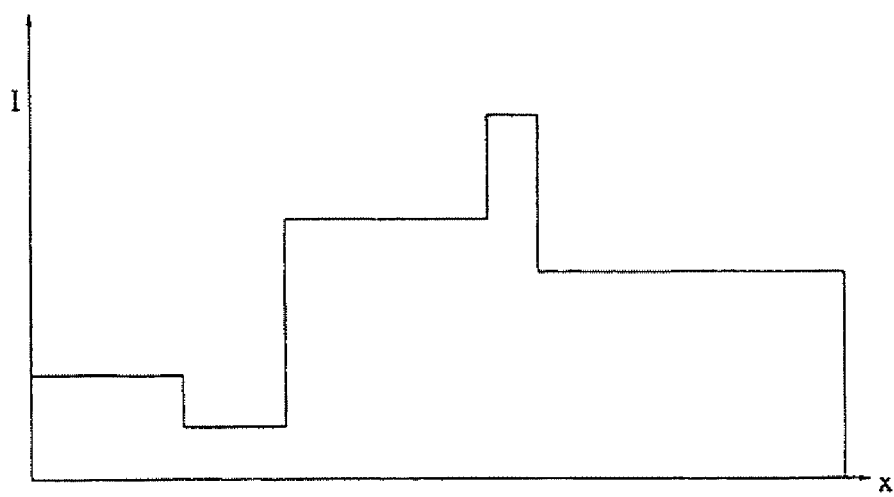
FIG. 6 shows a single pair profile.

Consider the problem of splitting a single leaf pair profile I (FIG. 6) into three fields. In the discussion below, the indices are calculated assuming that $2w < g \leq 3w$. However, the method can easily be used for $g \leq 2w$ with some modifications. The method we describe is an extension of the method used for splits into two. Denote the three fields resulting from the split as left, middle and right fields. As in case of the split into two, the left field can extend over the points $x_1, x_2, \ldots, x_w$, and the right field can extend over $x_{g-w+1}, x_{g-w+2}, \ldots, x_g$. For the position of the middle profile, there are several possibilities within a range. We examine each one of these and select the best.

The left most sample point that can be exposed in the middle field is $x_{g-2w+1}$. When $x_{g-2w+1}$ is included in the middle field, the middle field can extend over $x_{g-2w+1}, x_{g-2w+2}, \ldots x_{g-w}$. In this case, the w points $x_{g-w+1}, x_{g-w+2}, \ldots, x_g$, are treated by the right profile and so the middle profile cannot be any further to the left, without leaving at least the point $x_{g-w}$ not treated. Shifting the left boundary of the middle field one sample point to the right, the middle profile can extend over $x_{g-2w+2}, x_{g-2w+3}, \ldots, x_{g-w+1}$. Proceeding in this manner, it is clear that the left most position included in the middle profile has to be one of the following: $x_{g-w+1}, x_{g-w+2}, \ldots, x_{w+1}$. Algorithm S3G determines the optimal total therapy time separately assuming each one of these is necessarily the left most in the middle profile. The global optimum will be the least among these times. Next we explain how we find the optimal therapy time when a point $x_j$ is the left most point in the middle profile.

Figure 7:
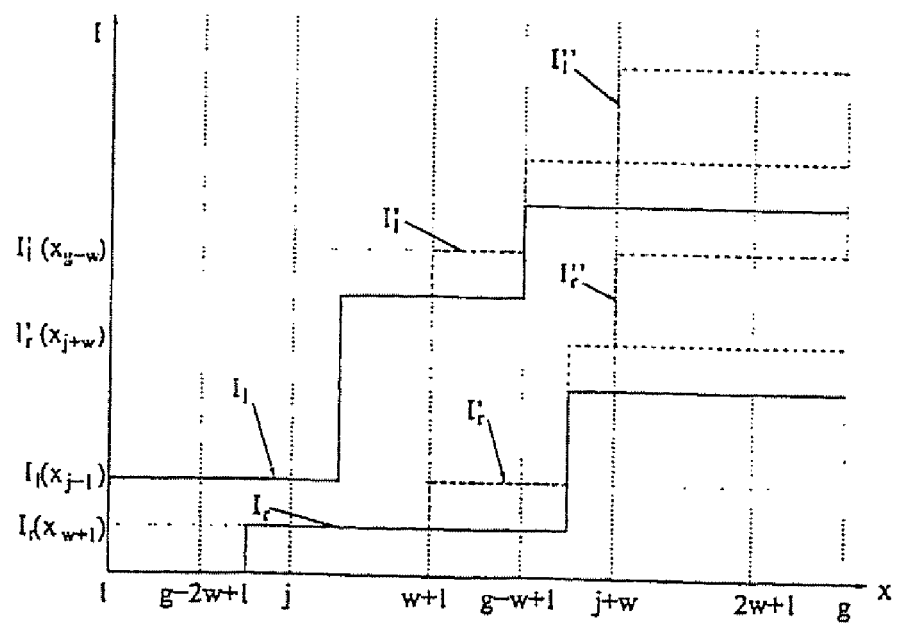
FIG. 7 shows Plan $(I_l, I_r)$, for profile I of FIG. 6, is obtained using Algorithm SINGLEPAIR and is constructed without taking field width constraints into account. $(I''_l, I''_r)$ is the modified plan obtained during an iteration of Algorithm S3G with $x_j$ as shown.
Figure 8:
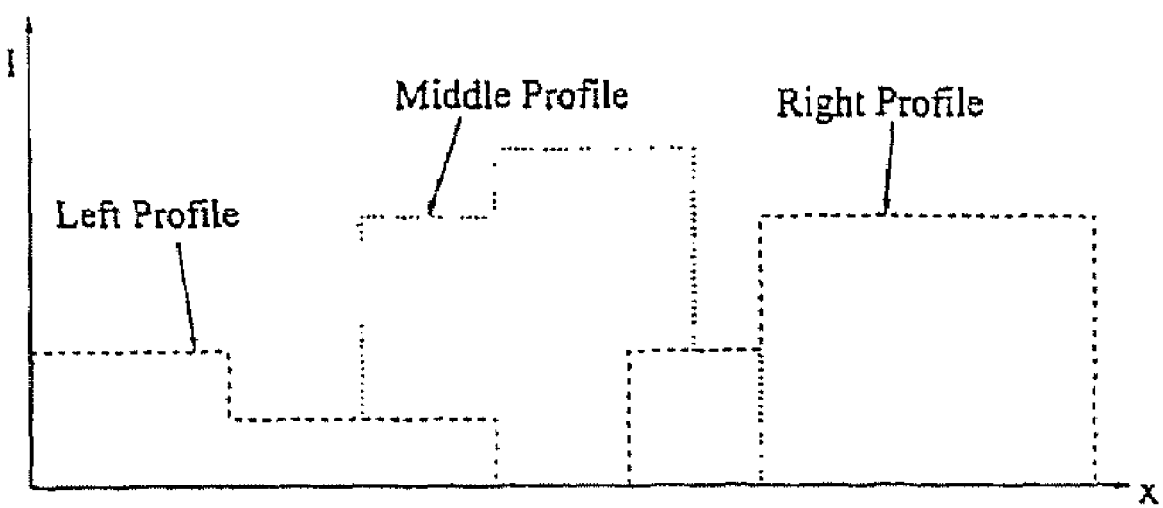
FIG. 8 shows The left and right profiles resulting from the split generated during the iteration of Algorithm S3G shown in FIG. 7. This split is delivered in optimal time using the plan $(I''_l, I''_r)$.

Suppose that the left most point of the middle profile is $x_j$, i.e., $x_j$ is necessarily part of the middle profile. First construct the trajectories for the left and right leaves assuming I is treated using one field (FIG. 7). Next, examine this plan $(I_l, I_r)$ and determine whether $I_l(x_{j-1}) < I_r(x_{w+1})$. If this is the case, start treatment of the left field with both leaves at the extreme left and move to the middle field when the left leaf reaches $x_j$ in the left to right sweep. Otherwise, stop the right leaf at $x_{w+1}$ till the left leaf reaches $x_j$. As a result of this action, the right leaf profile gets raised by an amount $I_l(x_{j-1}) - I_r(x_{w+1})$ for $x \geq x_{w+1}$. Raise the left leaf profile by the same amount for $x \geq x_{w+1}$ to account for the difference between the profiles. Call this modified plan $(I'_l, I'_r)$. In the plan $(I'_l, I'_r)$ see if $I'_l(x_{g-w}) \leq I'_r(x_{j+w})$. If this is the case, stop treating the middle field and move to the right field when the left leaf reaches $x_{g-w+1}$ during the sweep. Otherwise, stop the right leaf at sample point $x_{j+w}$ till the left leaf reaches $x_{g-w+1}$. The right leaf profile $I'_r$ gets raised by an amount $I'_l(x_{g-w}) - I'_r(x_{j+w})$ for $x \geq x_{j+w}$. The left leaf profile $I'_l$ is also raised by $I'_l(x_{g-w}) - I'_r(x_{w+1})$ for $x \geq x_{j+w}$. The resulting plan is denoted by $(I''_l, I''_r)$. We show that the split generated as a result of this method is optimal in total therapy time for all cases where the middle profile has $x_j$ as its left most point. The split generated for the profile of FIG. 6 with the $x_j$ as in FIG. 7 is shown in FIG. 8.

Algorithm S3G (1) Find plan $(I_l, I_r)$ for I using Algorithm SINGLEPAIR ignoring the field width constraints.
(2) For j=g−2w+1 to w+1 do steps 3 through 5.
(3) If $I_l(x_{j-1}) > I_r(x_{w+1})$, raise the left and right leaf profiles by $I_l(x_{j-1}) - I_r(x_{w+1})$ for $x > x_w$. Otherwise, do not modify the plan. Call the resulting plan $(I'_l, I'_r)$
(4) If $I'_l(x_{g-w}) > I'_r(x_{j+w})$, raise the left and right leaf profiles by $I'_l(x_{g-w}) - I'_r(x_{j+w})$ for $x \geq x_{j+w}$. Otherwise, do not modify the plan. Call the resulting plan $(I''_l, I''_r)$.
(5) If $TT(I''_l, I''_r)$ is the least among all j so far, set j'=j.
(6) Treat the profile using the plan $(I''_l, I''_r)$ obtained using j=j'. Treat the left field for the first $I''_l(x_{j-1})$ MUs; then move to the middle field; finally, switch to the right field when $I''_l(x_{g-w})$ MUs have been delivered.

Optimal Generalized Split for Splitting a Profile into Three

Again, we compute the indices assuming that $2w < g \leq 3w$. In general the method can also be used for $g \leq 2w$. As in the case of single leaf pair, the left most position included in the middle profile has to be one of the following: $x_{g-2w+1}, x_{g-2w+2}, \ldots x_{w+1}$. The optimal total therapy time is separately found assuming each one of these points is necessarily the left most in the middle profile. The optimal total therapy time will be the least among these.

Assume that the left most point of the middle profile is $x_j$, $g-2w+1 \leq j \leq w+1$. The points $x_1, x_2, \ldots, x_{j-1}$, need to be completely treated in the left field. Let k be an index of a left pair for which the left leaf is slowest in reaching $x_j$ during the left to right sweep, i.e., $I_{kl}(x_{j-1}) = \max_{1 \leq i \leq n} \{ I_{il}(x_{j-1}) \}$. For each leaf pair i, compare $I_{ir}(x_{w+1})$ with $I_{kl}(x_{j-1})$. If $I_{kl}(x_{j-1}) \leq I_{ir}(x_{w+1})$, then the profile of leaf pair i remains unaltered. On the other hand, if $I_{kl}(x_{j-1}) > I_{ir}(x_{w+1})$, then the right leaf of pair i will have to stop at $x_{w+1}$ till the left leaf of pair k arrives at $x_j$. As a result, the left and right leaf profiles of pair i get raised by $I_{kl}(x_{j-1}) - I_{ir}(x_{w+1})$ for $x > x_w$. Call this modified schedule $\{(I'_{1l}, I'_{1r}), (I'_{2l}, I'_{2r}), \ldots, (I'_{nl}, I'_{nr})\}$. Move to treatment of the middle field when the left leaf of pair k arrives at $x_j$ in this schedule. Note that the middle field can extend up to $x_{j+w-1}$ on the right and that the left most point of the right field is $x_{g-w+1}$. Modify the schedule $\{(I'_{1l}, I'_{1r}), (I'_{2l}, I'_{2r}), \ldots, (I'_{nl}, I'_{nr})\}$ as before so that the treatment of the right field begins when the slowest left leaf reaches $x_{g-w+1}$. The final schedule is $\{(I''_{1l}, I''_{1r}), (I''_{2l}, I''_{2r}), \ldots, (I''_{nl}, I''_{nr})\}$ The split generated as a result of this method is optimal in total therapy time for all cases where the middle profile has $x_j$ as its left most point. Algorithm M3G varies j over g−2w+1, g−2w+2, . . . , w+1, and finds the best split.

Algorithm M3G (1) Find the schedule $\{(I_{1l},I_{1r}), (I_{2l},I_{2r}), \ldots, (I_{nl},I_{nr})\}$ for I using Algorithm MULTIPAIR, ignoring the field width constraints.
(2) For j=g−2w+1 to w+1 do steps 3 through 8.
(3) Let $I_{kl}(x_{j-1}) = \max_{1 \leq i \leq w}\{I_{il}(x_{j-1})\}$.
(4) For each leaf pair i do step 5.
(5) If $I_{kl}(x_{j-1}) > I_{ir}(x_{w+1})$, raise the left and right profiles of pair i by $I_{kl}(x_{j-1}) - I_{ir}(x_{w+1})$ for $x > x_w$. Otherwise, do not modify the plan for pair i.
(6) Call the resulting schedule $\{(I'_{1l},I'_{1r}), (I'_{2l},I'_{2r}), \ldots, (I'_{nl},I'_{nr})\}$.
(7) For each leaf pair i do step 8.
(8) If $I'_{kl}(x_{g-w}) > I'_r(x_{j+w})$, raise the left and right profiles of pair i by $I'_{kl}(x_{g-w}) - I'_{ir}(x_{j+w})$ for $x > x_{j+w}$. Otherwise, do not modify the plan for pair i.
(9) Call the resulting schedule $\{(I''_{1l},I''_{1r}), (I''_{2l},I''_{2r}), \ldots, (I''_{nl},I''_{nr})\}$.
(10) If $TT\{(I''_{1l},I''_{1r}), (I''_{2l},I''_{2r}), \ldots, (I''_{nl},I''_{nr})\}$ is the least among all j so far, j=j'.
(11) Treat the left field using the schedule $\{(I''_{1l},I''_{1r}), (I''_{2l},I''_{2r}), \ldots, (I''_{nl},I''_{nr})\}$ which is obtained using j=j' for $I''_{kl}(x_{j-1})$ MUs. Then switch to the right field and continue treatment with this schedule till $I'_{kl}(x_{g-w})$ MUs. Finally, move to the right field and complete the treatment.

EXAMPLES

The present invention is further illustrated by the following specific examples, which should not be construed as limiting the scope or content of the invention in any way.

Results based on variably feathering according to the invention is described below. The performance of the Algorithms M2G was tested using 32 clinical fluence matrices, each of which exceeded the maximum allowable field width w. The fluence matrices were generated with a commercial inverse treatment planning system (CORVUS v5.0). The percent decrease in MUs as a result of optimal field splitting over the split generated by the commercial system were computed. The average decrease in MUs is 19% for the 32 fluence matrices. The maximum decrease in MUs is 45%. All the subfields overlap to various degrees, creating a natural feathering area which is clinically desirable.

This invention has been described herein in considerable detail to provide those skilled in the art with information relevant to apply the novel principles and to construct and use such specialized components as are required. However, it is to be understood that the invention can be carried out by different equipment, materials and devices, and that various modifications, both as to the equipment and operating procedures, can be accomplished without departing from the scope of the invention itself.

We claim:

1. A method of delivering intensity-modulated radiation therapy (IMRT) using variable feathering field splitting for intensity modulated fields of large size, comprising the steps of:
   (a) providing an intensity matrix for the treatment of a patient, said intensity matrix having a plurality of rows and columns for spanning a prescribed radiation field including a prescribed field width;
   (b) comparing said prescribed width to a maximum field width provided by a radiation treatment system;
   (c) splitting said intensity matrix into a plurality of spatially overlapping intensity submatrices when said prescribed width exceeds said maximum field width, wherein said splitting comprises variably feathering said intensity matrix, and
   (d) providing radiotherapy to said patient using a leaf sequencing method applied to a beam-shaping device to generate said submatrices.

2. The method of claim 1, wherein said variably feathering comprises feathering along non-constant columns of said intensity matrix.

3. The method of claim 1, wherein said splitting is implemented by minimizing total therapy time.

4. The method of claim 1, wherein said splitting is implemented by minimizing a total number of leaf sequences in delivering a predetermined dosage to said patient.

5. The method of claim 1, wherein said beam-shaping device is a segmented multi-leaf collimator.

6. The method of claim 1, wherein said beam-shaping device is a dynamic multi-leaf collimator.

7. A system for delivering radiation treatment to patients, the system comprising:
   a radiation source for providing a radiation beam;
   a beam-shaping device interposed between the radiation source and a patient for shaping the radiation beam, the beam-shaping device having a plurality of leaves that cooperatively form leaf sequences for shaping the radiation beam, and
   a processor in communication with the beam-shaping device, said processor acting on an intensity matrix for the treatment of a patient, said intensity matrix having a plurality of rows and columns for spanning a prescribed radiation field including a prescribed field width, said processor causing the beam-shaping device to split the radiation beam into a plurality of spatially overlapping intensity submatrices that are delivered to said patient when said prescribed width exceeds a maximum field width provided by said system, wherein said splitting comprises variably feathering said intensity matrix.

8. The system of claim 7, wherein the beam-shaping device is a segmented multi-leaf collimator.

9. The system of claim 7, wherein the beam-shaping device is a dynamic multi-leaf collimator.

* * * * *

UNITED STATES PATENT AND TRADEMARK OFFICE
CERTIFICATE OF CORRECTION

PATENT NO. : 7,573,978 B2
APPLICATION NO. : 11/995303
DATED : August 11, 2009
INVENTOR(S) : Srijit Kamath et al.

It is certified that error appears in the above-identified patent and that said Letters Patent is hereby corrected as shown below:

Cover page, (57) Abstract,
Line 1, "system 300 for delivering" should read --system for delivering--.
Line 11, "width is compared to a" should read --width is compared to the--.

Column 1,
Lines 65-66, "With , the beams" should read --With IMRT, the beams--.

Column 2,
Lines 1-2, "As a result, is" should read --As a result, IMRT is--.
Line 2, "because can" should read --because IMRT can--.
Lines 7-8, "radiation results in dose being in absorbed in" should read --radiation results in the dose being absorbed in--.
Line 11, "successful program." should read --successful IMRT program--.
Line 23, "can be" should read --IMRT can be--.
Line 40, "Most treatments" should read --Most IMRT treatments--.
Line 53, "fields portions," should read --field portions,--.
Line 60, "dose in delivery," should read --dose in IMRT delivery,--.

Column 3,
Line 54, "MUs in the leftfield" should read --MUs in the left field--.

Column 4,
Line 38, "beam-shaping-device" should read --beam-shaping device--.
Line 53, "no more 20 percent" should read --no more than 20 percent--.

Column 5,
Lines 59-60, "conventional t commercial system." should read --conventional commercial system--.

Signed and Sealed this
Nineteenth Day of July, 2011

David J. Kappos
*Director of the United States Patent and Trademark Office*

CERTIFICATE OF CORRECTION (continued)
U.S. Pat. No. 7,573,978 B2

Column 7,
Lines 19-20, "move to the right field and continue" should read --moved to the right field and continues--.

Lines 52-54,
"Treat the left field using the plan $(I_l,I_r)$ for $I_l(x_{g-w})$ MUs.
Then switch to the right field and continue treatment with
$(I_l,I_r)$." should read --Treat the left field using the plan $(I_l,I_{r'})$ for $I_l(x_{g-w})$ MUs.
  Then switch to the right field and continue treatment
    with $(I_l,I_r)$.--

Column 10,
Line 14, "$(x_{j+w+1})$" should read --$(x_{j+w-1})$--.

Column 11,
Line 6, "$=\max_{1 \le i \le w}$" should read --$=\max_{1 \le i \le n}$--.
Line 16, "$>I'_r(x_{f+w})$" should read -->$I'_{ir}(x_{j+w})$--.

UNITED STATES PATENT AND TRADEMARK OFFICE
CERTIFICATE OF CORRECTION

| | | |
|---|---|---|
| PATENT NO. | : 7,573,978 B2 | Page 1 of 1 |
| APPLICATION NO. | : 11/995303 | |
| DATED | : August 11, 2009 | |
| INVENTOR(S) | : Srijit Kamath et al. | |

It is certified that error appears in the above-identified patent and that said Letters Patent is hereby corrected as shown below:

In the Specification:

At column 1, line 18, please correct the Government NIH Grant/Contract No. "LM06659-03" which should be corrected to read --LM0006659-03--

Signed and Sealed this
Twenty-fourth Day of May, 2016

Michelle K. Lee
*Director of the United States Patent and Trademark Office*